(12) United States Patent
Sakashita et al.

(10) Patent No.: US 10,174,698 B2
(45) Date of Patent: Jan. 8, 2019

(54) HEATER CONTROL DEVICE FOR EXHAUST GAS SENSOR

(71) Applicant: DENSO CORPORATION, Kariya, Aichi-pref. (JP)

(72) Inventors: Yoshihiro Sakashita, Kariya (JP); Yukihiro Yamashita, Kariya (JP); Ryozo Kayama, Kariya (JP)

(73) Assignee: DENSO CORPORATION, Kariya (JP)

( * ) Notice: Subject to any disclaimer, the term of this patent is extended or adjusted under 35 U.S.C. 154(b) by 9 days.

(21) Appl. No.: 15/120,615

(22) PCT Filed: Apr. 8, 2015

(86) PCT No.: PCT/JP2015/001980
§ 371 (c)(1),
(2) Date: Aug. 22, 2016

(87) PCT Pub. No.: WO2015/162865
PCT Pub. Date: Oct. 29, 2015

(65) Prior Publication Data
US 2017/0009685 A1    Jan. 12, 2017

(30) Foreign Application Priority Data
Apr. 21, 2014 (JP) .................. 2014-087769

(51) Int. Cl.
*F02D 41/06* (2006.01)
*F02D 41/14* (2006.01)
(Continued)

(52) U.S. Cl.
CPC ......... *F02D 41/064* (2013.01); *F02D 41/146* (2013.01); *F02D 41/1461* (2013.01);
(Continued)

(58) Field of Classification Search
CPC .. F02D 41/064; F02D 41/146; F02D 41/1461; F02D 41/1494; G01N 27/416; G01N 27/417
See application file for complete search history.

(56) References Cited

U.S. PATENT DOCUMENTS 5,719,778 A * 2/1998 Suzumura .......... G01N 27/4067
700/207
6,870,142 B2 * 3/2005 Hada .................... F02D 41/1494
219/494
(Continued)

FOREIGN PATENT DOCUMENTS

DE  102012008462 A1 * 10/2012 ............ F01N 11/002
JP  2003-166967        6/2003
(Continued)

*Primary Examiner* — Phutthiwat Wongwian
*Assistant Examiner* — Matthew T Largi
(74) *Attorney, Agent, or Firm* — Nixon & Vanderhye P.C.

(57) ABSTRACT

A heater control device for an exhaust gas sensor disposed in an exhaust gas passage of an internal combustion engine and including a sensor element having a plurality of cells, and a heater heating the sensor element includes: a heater power control unit configured to execute a temp rising control, in which an impedance of one cell to be measured, of the plurality of cells, is detected and a temperature of the sensor element is raised until the impedance of the one cell reaches a target impedance by setting a power control value of the heater as a heating power control value. The heater power control unit continues the temp rising control until an extension period elapses that is needed for the other cell other than the one cell to reach an activation temperature after the impedance of the one cell reaches the target impedance.

7 Claims, 4 Drawing Sheets

(51) Int. Cl.
*G01N 27/417* (2006.01)
*G01N 27/406* (2006.01)

(52) U.S. Cl.
CPC ..... *F02D 41/1494* (2013.01); *G01N 27/4067* (2013.01); *G01N 27/417* (2013.01)

(56) References Cited

U.S. PATENT DOCUMENTS

| | | | | |
|---|---|---|---|---|
| 2005/0029250 | A1* | 2/2005 | Niwa | F02D 41/1494 219/494 |
| 2009/0051373 | A1* | 2/2009 | Kato | G01N 27/4065 324/693 |
| 2017/0074147 | A1* | 3/2017 | Sakashita | F01N 11/002 |

FOREIGN PATENT DOCUMENTS

| | | |
|---|---|---|
| JP | 2009-288082 | 12/2009 |
| JP | 2009288082 A * | 12/2009 |

* cited by examiner

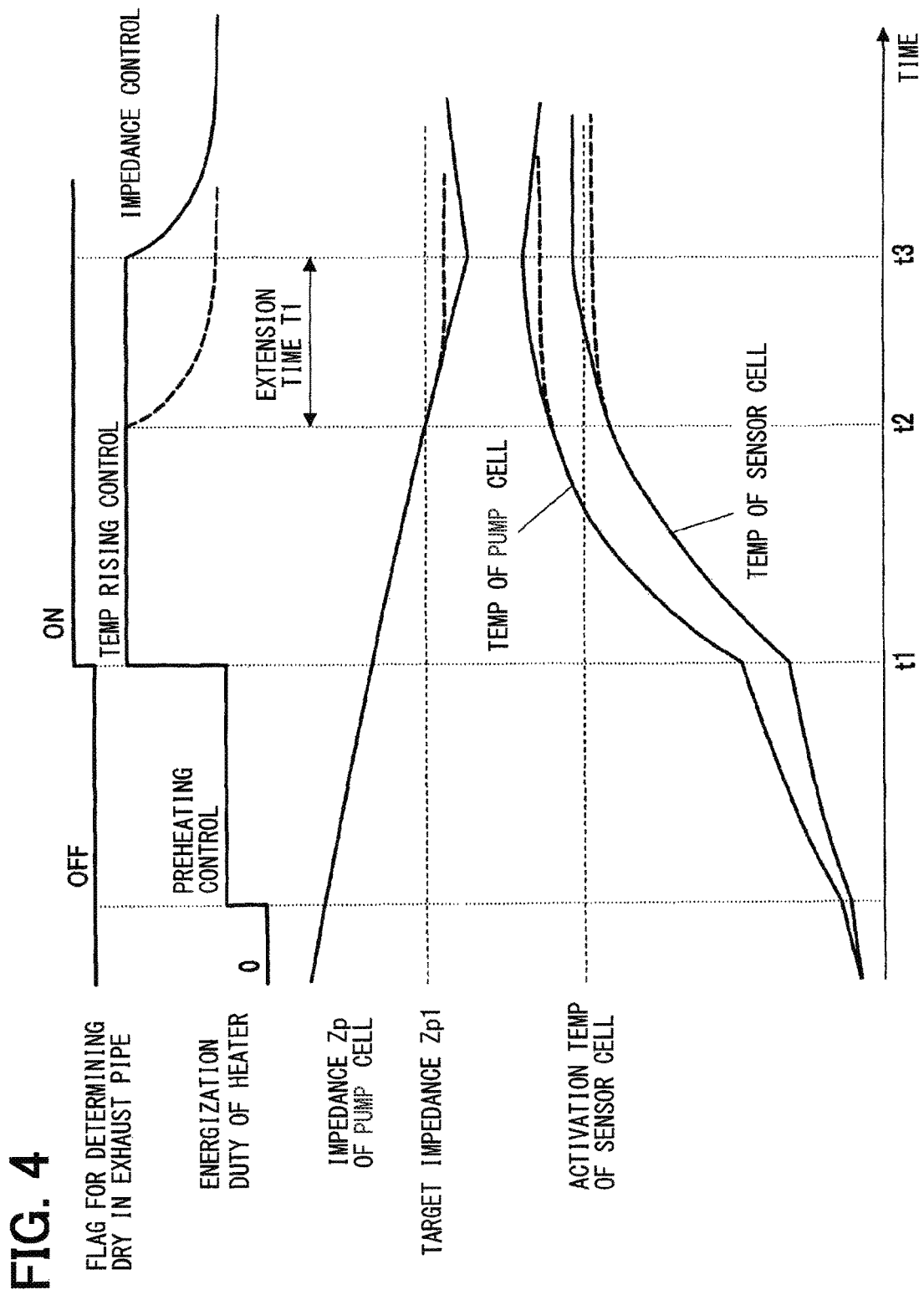

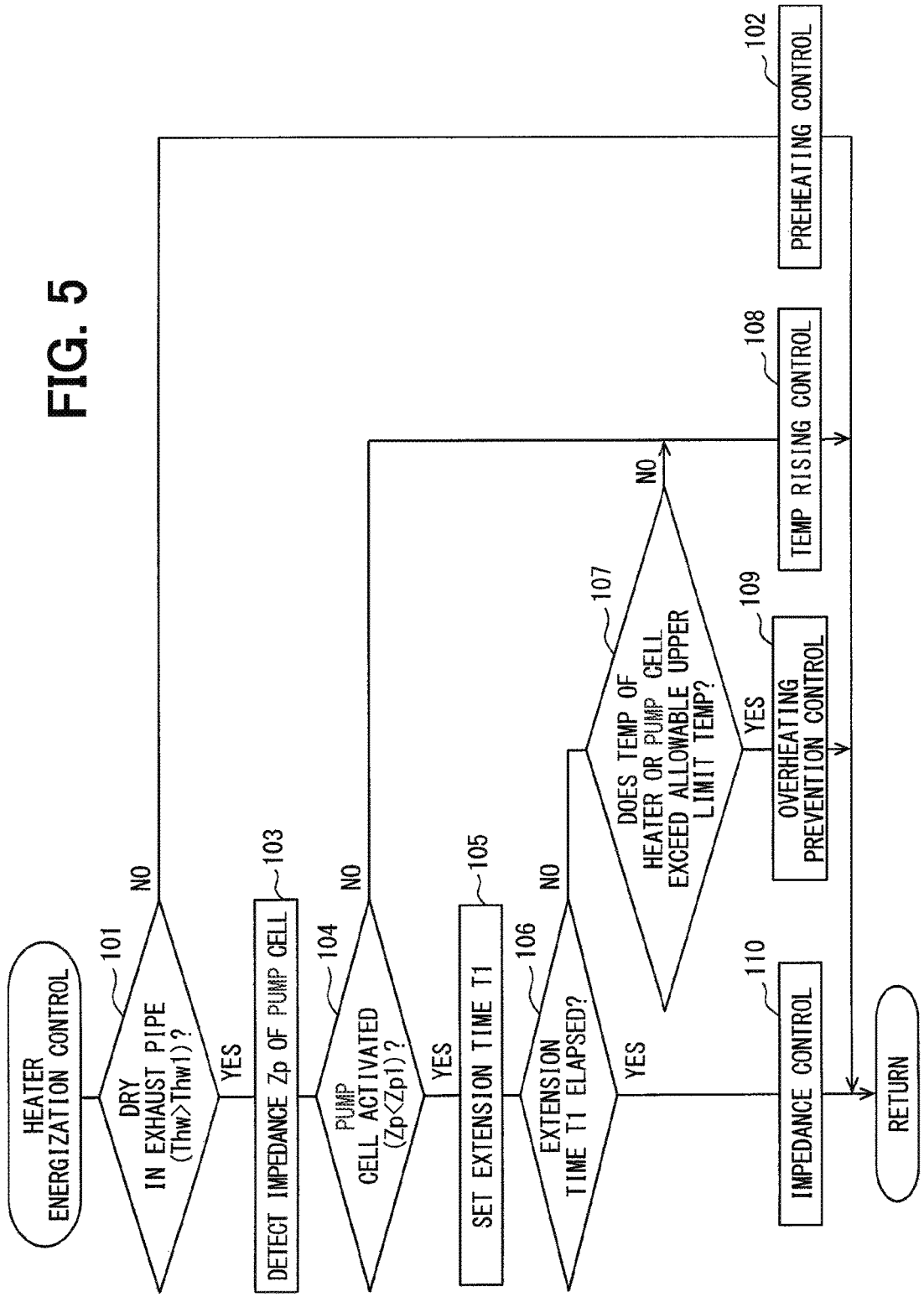

HEATER CONTROL DEVICE FOR EXHAUST GAS SENSOR

CROSS REFERENCE TO RELATED APPLICATION

This application is the U.S. national phase of International Application No. PCT/JP2015/001980 filed Apr. 8, 2015, which designated the U.S. and claims priority to Japanese Patent Application No. 2014-87769 filed on Apr. 21, 2014, the entire contents of each of which are hereby incorporated herein by reference.

TECHNICAL FIELD

The present disclosure relates to a heater control device for an exhaust gas sensor including a sensor element having a plurality of cells and a heater heating the sensor element.

BACKGROUND ART

Electronically-controlled internal combustion engines available in recent years control an air-fuel ratio and the like on the basis of the output of an exhaust gas sensor placed in an exhaust pipe. Exhaust gas sensors generally exhibit poor sensing precision (or fail to function) before the sensor elements achieve activation temperatures. Hence, a heater inside an exhaust gas sensor is used to heat its sensor element after the start of the internal combustion engine in order to activate the exhaust gas sensor.

A known type of exhaust gas sensors (for example, $NO_X$ sensors) is provided with a sensor element including a plurality of cells. Systems are available that control the power to the heater such that an impedance (internal resistance) measured from one of the cells as temperature information reaches a target impedance that corresponds to the activation temperature of the cell measured.

The cells have different activation temperatures; thus, by controlling the power to the heater such that the impedance of only the cell measured reaches a target impedance, the temperature of another cell may not reach its activation temperature.

In Patent Literature 1, the power to the heater is controlled such that the resistance value of a cell to be measured achieves a first predetermined resistance value. Then, the power to the heater is further controlled such that the resistance value of the cell to be measured achieves a second predetermined resistance value that is greater than the first predetermined resistance value.

PRIOR ART LITERATURES

Patent Literature

Patent Literature 1: JP 2009-69140 A

SUMMARY OF INVENTION

The power to the heater is controlled such that the second predetermined resistance value that corresponds to a temperature lower than a temperature corresponding to the first predetermined resistance value is achieved in Patent Literature 1; thus, another cell may not quickly be activated (it may not achieve its activation temperature). If the output of the exhaust gas sensor is used with the other cell insufficiently activated, control (for example, urea injection control) and diagnosis (for example, catalyst degradation diagnosis) based on the output of the exhaust gas sensor (for example, $NO_X$ sensor) may not be performed properly.

An object of the present disclosure is to provide a heater control device for an exhaust gas sensor provided with a sensor element including a plurality of cells, one of the cells being a cell to be measured (a cell from which an impedance is detected), the heater control device being capable of quickly activating another cell.

According to an aspect of the present disclosure, a heater control device for an exhaust gas sensor disposed in an exhaust gas passage of an internal combustion engine and including a sensor element having a plurality of cells, and a heater heating the sensor element includes: a heater power control unit configured to execute a temp rising control, in which an impedance of one cell to be measured, of the plurality of cells, is detected and a temperature of the sensor element is raised until the impedance of the one cell reaches a target impedance by setting a power control value of the heater as a heating power control value. The heater power control unit continues the temp rising control after the impedance of the one cell reaches the target impedance until an extension period elapses that is needed for the other cell other than the one cell to reach an activation temperature.

In order to activate the sensor element of the exhaust gas sensor, the temp rising control is executed to raise the temperature of the sensor element until the impedance of the one cell reaches the target impedance (for example, a value corresponding to the activation temperature of the one cell). The temp rising control is further continued until the extension period elapses that is needed for another cell to achieve its activation temperature after the impedance of the one cell reaches the target impedance. The temp rising control to raise the temperature of the sensor element is continued after the one cell achieves its activation temperature; in this manner, the other cell is enabled to achieve its activation temperature quickly and thereby to be quickly activated.

BRIEF DESCRIPTION OF DRAWINGS

FIG. 4 is a time chart of exemplary heater power control.

FIG. 5 is a flowchart of a procedure of a heater power control routine.

DESCRIPTION OF EMBODIMENTS

Hereinafter, an embodiment will be described according to the drawings.

Figure 1:
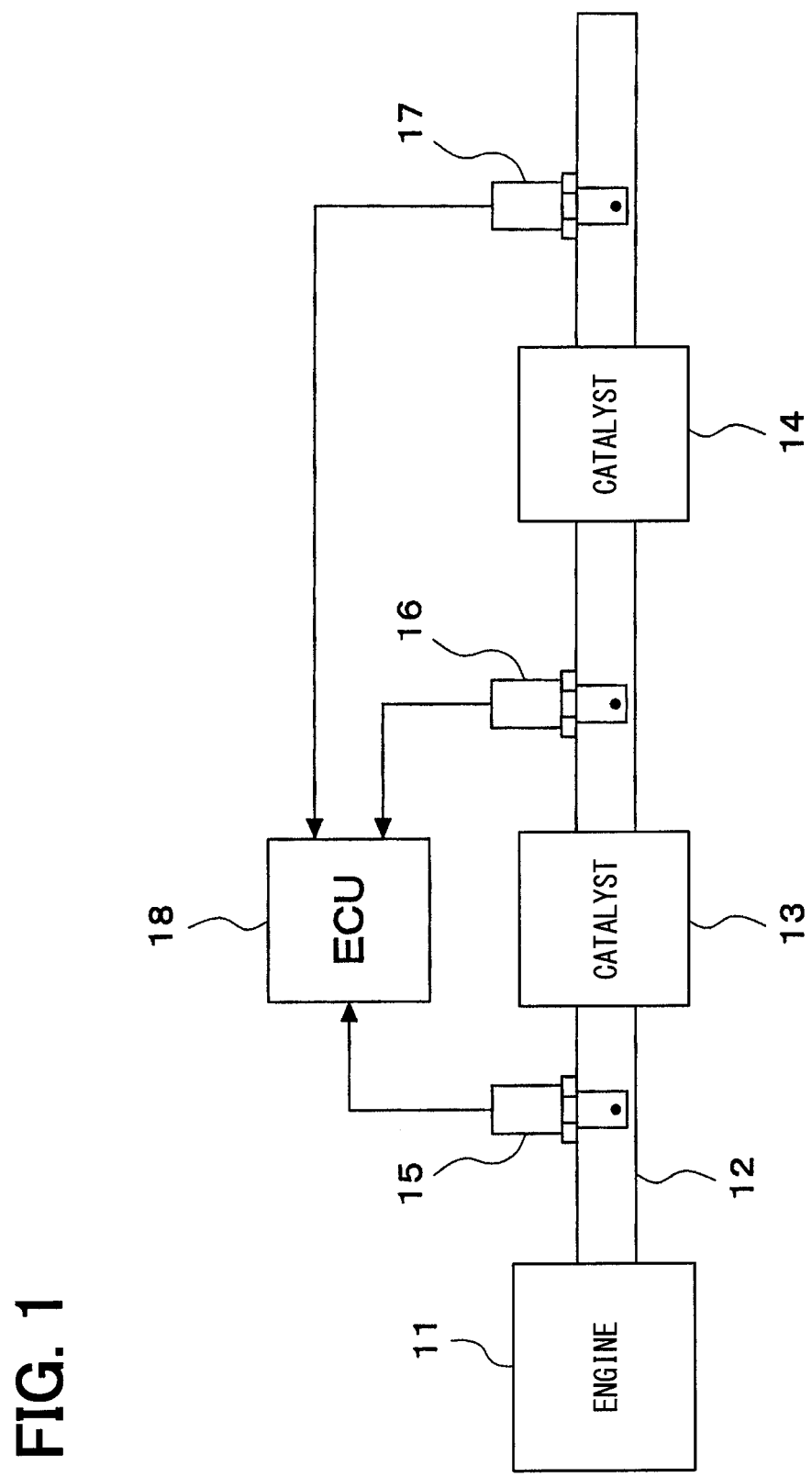
FIG. 1 is a diagram of a schematic configuration of an engine control system according to an embodiment of the present disclosure.

A schematic configuration of an engine control system is described with reference to FIG. 1.

An engine 11, which is an internal combustion engine, is provided with an exhaust pipe 12 (an exhaust gas passage), and the exhaust pipe 12 is provided with an upstream catalyst 13 and a downstream catalyst 14, which may be three-way catalysts for removal of CO, HC, $NO_X$, and the like from an exhaust gas. An air-fuel ratio sensor 15 is disposed upstream of the upstream catalyst 13 to detect the air-fuel ratio of the exhaust gas. An oxygen sensor 16 is placed downstream of the upstream catalyst 13 (between the upstream catalyst 13 and the downstream catalyst 14) to determine the richness/leanness of the exhaust gas. A $NO_X$ sensor 17 is disposed downstream of the downstream catalyst 14 to detect the concentration of $NO_X$ in the exhaust gas.

The outputs of the sensors 15, 16, and 17 are input to an electronic control unit (hereinafter referred to as ECU) 18. The ECU 18 includes a microcomputer, which is its main component, and controls fuel injection quantity, ignition timing, throttle opening (intake air quantity), and other factors in accordance with the operating state of the engine by executing various engine control programs stored in a built-in ROM (a storage medium).

Figure 2:
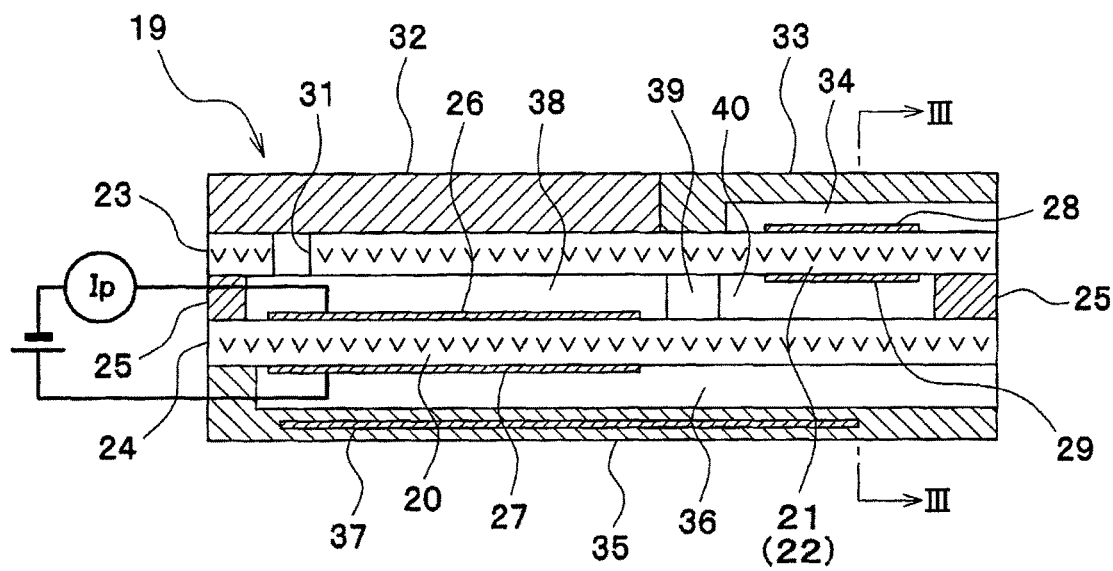
FIG. 2 is a sectional view of a sensor element, illustrating its schematic configuration.
Figure 3:
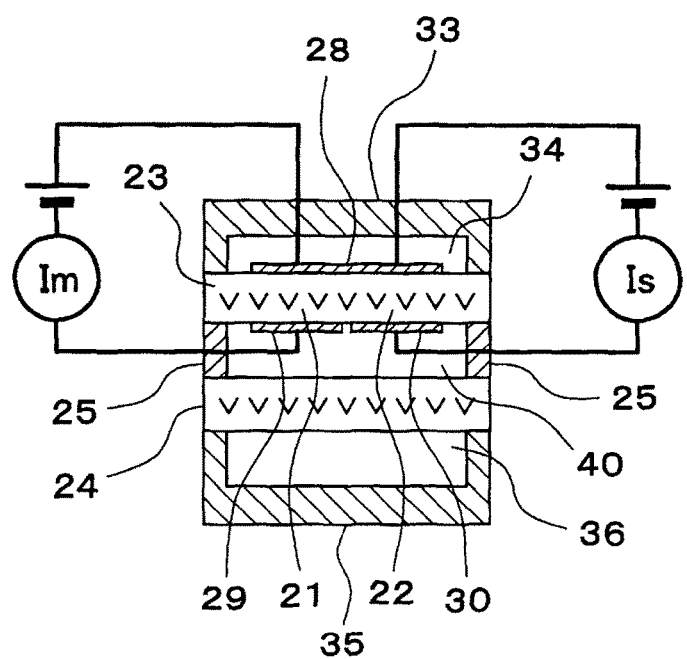
FIG. 3 is a cross-sectional view taken along a line III-III in FIG. 2.

With reference to FIGS. 2 and 3, a schematic configuration of a sensor element 19 of the $NO_X$ sensor 17 is described below.

The sensor element 19 of the $NO_X$ sensor 17 has a three cell structure including a pump cell 20, a monitor cell 21, and a sensor cell 22. The sensor element 19 includes layers of first and second solid electrolytes 23 and 24, which are made of an oxygen ion conductive material, and a spacer 25, which is made of an insulating material, such as alumina. The first and second solid electrolytes 23 and 24 are spaced apart from each other by a predetermined interval with the spacer 25 interposed between the first and second solid electrolytes 23 and 24.

The pump cell 20 includes the second solid electrolyte 24 and a pair of electrodes 26 and 27, with the second solid electrolyte 24 interposed between the electrodes 26 and 27. The monitor cell 21 includes the first solid electrolyte 23 and a pair of electrodes 28 and 29, with the first solid electrolyte 23 interposed between the electrodes 28 and 29. The sensor cell 22 includes the first solid electrolyte 23, the electrode 28, and an electrode 30, with the first solid electrolyte 23 interposed between the electrodes 28 and 30. That is, the monitor cell 21 and the sensor cell 22 share the electrode 28.

The first solid electrolyte 23 has a pinhole 31. A porous diffusion layer 32 is placed on an upper surface of the first solid electrolyte 23 where the pump cell 20 is located. An insulating layer 33 is placed on the upper surface of the first solid electrolyte 23 where the monitor cell 21 and the sensor cell 22 are located. The insulating layer 33 forms an atmosphere passage 34. An insulating layer 35 is placed on a lower surface of the second solid electrolyte 24. The insulating layer 35 forms an atmosphere passage 36. The insulating layer 35 includes a heater 37 therein to heat up the sensor element 19.

The exhaust gas in the exhaust pipe 12 passes through the porous diffusion layer 32 and the pinhole 31 formed in the solid electrolyte 23 to enter a first chamber 38. The pump cell 20 discharges or draws oxygen in the exhaust gas relative to the first chamber 38 and detects an oxygen concentration in the exhaust gas. Then, the exhaust gas in the first chamber 38 passes through an orifice 39 into a second chamber 40. The monitor cell 21 detects an oxygen concentration (a residual oxygen concentration) in the exhaust gas in the second chamber 40. The sensor cell 22 detects a $NO_X$ concentration in the exhaust gas in the second chamber 40.

The $NO_X$ sensor 17 generally exhibits poor sensing precision (or fails to function) before the sensor element 19 (at the cells 20 to 22) achieves activation temperatures. Thus, by executing a heater power control routine in FIG. 5 to be described hereinafter, the ECU 18 controls power to the heater 37 inside the $NO_X$ sensor 17 to heat up and thereby activate the sensor element 19.

Specifically, as illustrated in FIG. 4, after the start of the engine 11, for example, it is determined whether the inside of the exhaust pipe 12 is dry (whether moisture in the exhaust pipe 12 has been vaporized). When it is determined that the inside of the exhaust pipe 12 is not dry (an exhaust pipe dry determination flag is OFF), moisture may be on the exhaust pipe 12 and the $NO_X$ sensor 17, and preheating control is executed. In the preheating control, the power to the heater 37 is controlled such that the sensor element 19 of the $NO_X$ sensor 17 is preheated in a temperature range in which no crack due to water is caused to the element. In the preheating control, the sensor element 19 is preheated with a power duty (a power control value) of the heater 37 set to a preheating power duty (for example, 10%).

Subsequently, at a point in time t1, when it is determined that the inside of the exhaust pipe 12 is dry (the exhaust pipe dry determination flag is ON), temp rising control is executed in which the power to the heater 37 is controlled such that the temperature of the sensor element 19 is increased quickly. In the temp rising control, the sensor element 19 is heated with the power duty of the heater 37 set to a heating power duty (for example, 100%).

It is determined whether the pump cell 20 (a cell to be measured) is activated (whether it has achieved its activation temperature) in accordance with whether an impedance Zp of the pump cell 20 is smaller than a target impedance Zp1 (a value corresponding to the activation temperature of the pump cell 20).

At a point in time t2, when it is determined that the impedance Zp of the pump cell 20 is smaller than the target impedance Zp1 and thus the pump cell 20 is activated, an extension time T1 needed for the sensor cell 22 (another cell) to achieve an activation temperature of the sensor cell 22 is set. Then, the temp rising control is continued from the point in time t2, when it is determined that the pump cell 20 is activated, until the extension time T1 elapses. In this manner, the sensor cell 22 achieves its activation temperature at an early timing.

At a point in time t3, when the extension time T1 has elapsed from the determination of the activation of the pump cell 20 at the point in time t2, it is deemed that the sensor cell 22 has achieved its activation temperature. The temp rising control is ended, and impedance control is executed in which the power to the heater 37 is controlled such that the active state of the sensor element 19 is maintained. In the impedance control, the power duty of the heater 37 is feedback-controlled such that the deviation between the impedance Zp of the pump cell 20 and a target impedance Zp1 is minimized. The target impedance Zp1 used in the impedance control may be set to a value corresponding to the activation temperature of the pump cell 20 or a value with which the sensor cell 22 can be maintained at the activation temperature of the sensor cell 22.

The heater power control routine in FIG. 5 to be executed by the ECU 18 is described below.

The heater power control routine illustrated in FIG. 5, which is repeated at a predetermined cycle while the power to the ECU 18 is on, serves as a heater power control unit.

When the routine is started, it is determined in step 101 whether the inside of the exhaust pipe 12 is dry (whether moisture in the exhaust pipe 12 has been vaporized) in accordance with, for example, whether a coolant temperature Thw has a value greater than a predetermined value Thw1.

When it is determined in step 101 that the inside of the exhaust pipe 12 is not dry (Thw≤Thw1), it is deemed that moisture may be on the exhaust pipe 12 and the $NO_X$ sensor 17. The flowchart proceeds to step 102, in which preheating control is executed. In the preheating control, the sensor element 19 is heated with the power duty of the heater 37 set to a preheating power duty (for example, 10%).

Subsequently, when it is determined in step 101 that the inside of the exhaust pipe 12 is dry (Thw>Thw1), the flowchart proceeds to step 103, in which the impedance Zp of the pump cell 20 is detected. The flowchart then proceeds to step 104, in which it is determined whether the pump cell 20 is activated (whether the pump cell 20 has achieved its activation temperature) in accordance with whether the impedance Zp of the pump cell 20 is smaller than a target impedance Zp1. The target impedance Zp1 is set to a value corresponding to the activation temperature of the pump cell 20.

When it is determined in step 104 that the pump cell 20 is not activated (Zp≥Zp1), the flowchart proceeds to step 108, in which the temp rising control is executed. In the temp rising control, the sensor element 19 is heated with the power duty of the heater 37 set to a heating power duty (for example, 100%).

Subsequently, when it is determined in step 104 that the pump cell 20 is activated (Zp<Zp1), the flowchart proceeds to step 105, in which the extension time T1 needed for the sensor cell 22 to achieve its activation temperature is set. Specifically, the extension time T1 in accordance with an operating condition of the engine 11 and an environmental condition is calculated using a map or a mathematical expression. As the operating condition, at least one of, for example, the coolant temperature, exhaust gas temperature, rotational speed, and load is used. As the environmental condition, outside air temperature, for example, is used. The map or the mathematical expression for the extension time T1 is generated in advance on the basis of test data and design data and stored in the ROM of the ECU 18.

The flowchart then proceeds to step 106, in which it is determined whether the extension time T1 has elapsed from the determination of the activation of the pump cell 20.

When it is determined in step 106 that the extension time T1 has not elapsed from the determination of the activation of the pump cell 20, the flowchart proceeds to step 107, in which it is determined whether the temperature of the heater 37 or the temperature of the pump cell 20 is likely to exceed a corresponding tolerable upper-limit temperature.

Here, for example, the temperature of the heater 37 is estimated (calculated) on the basis of the integral power consumption and the resistance of the heater 37. It is then determined whether the temperature of the heater 37 is likely to exceed the corresponding tolerable upper-limit temperature in accordance with whether the estimated temperature of the heater 37 is equal to or higher than a predetermined temperature (a temperature slightly lower than the tolerable upper-limit temperature of the heater 37).

The temperature of the pump cell 20 is estimated (calculated) on the basis of the impedance or the like of the pump cell 20. It is then determined whether the temperature of the pump cell 20 is likely to exceed the corresponding tolerable upper-limit temperature in accordance with whether the estimated temperature of the pump cell 20 is equal to or higher than a predetermined temperature (a temperature slightly lower than the tolerable upper-limit temperature of the pump cell 20). Alternatively, it may be determined whether the temperature of the pump cell 20 is likely to exceed the tolerable upper-limit temperature in accordance with whether the impedance of the pump cell 20 has a value equal to or less than a predetermined value.

When it is determined in step 107 that both of the temperatures of the heater 37 and the pump cell 20 are not likely to exceed the corresponding tolerable upper-limit temperatures, the flowchart proceeds to step 108, in which the temp rising control is continued.

Subsequently, when it is determined in step 106 that the extension time T1 has elapsed from the determination of the activation of the pump cell 20, it is deemed that the sensor cell 22 has achieved the activation temperature of the sensor cell 22. The flowchart proceeds to step 110, in which the impedance control is executed. In the impedance control, the power duty of the heater 37 is feedback-controlled such that the deviation between the impedance Zp of the pump cell 20 and a target impedance Zp1 is minimized. The target impedance Zp1 used in the impedance control may be set to a value corresponding to the activation temperature of the pump cell 20 or a value with which the sensor cell 22 can be maintained at the activation temperature of the sensor cell 22.

When it is determined in step 107 that the temperature of the heater 37 or the temperature of the pump cell 20 is likely to exceed the corresponding tolerable upper-limit temperature before it is determined that the extension time T1 has elapsed in step 106 (that is, during the temp rising control), the flowchart proceeds to step 109, in which the temp rising control is interrupted and overheating prevention control is executed. In the overheating prevention control, the rise of the temperature of the sensor element 19 is prevented with the power duty of the heater 37 set to a value less than a value of the heating power duty (for example, 30%).

In the embodiment described above, in order to activate the sensor element 19 of the $NO_X$ sensor 17, the temp rising control is executed to raise the temperature of the sensor element 19 until the impedance of the pump cell 20 reaches a target impedance. The temp rising control is further continued until an extension time elapses that is needed for the sensor cell 22 to achieve its activation temperature after the impedance of the pump cell 20 reaches the target impedance. In this manner, the sensor cell 22 can achieve its activation temperature at an earlier timing and thereby be activated at an earlier timing in comparison with the case where the temp rising control is ended at the point in time t2, when the impedance of the pump cell 20 achieves the target impedance (see dashed lines in FIG. 4).

Additionally, in the embodiment, when it is determined that the temperature of the heater 37 or the temperature of the pump cell 20 is likely to exceed a corresponding tolerable upper-limit temperature during the temp rising control, the temp rising control is interrupted and the overheating prevention control is executed (in which the power duty of the heater 37 is set to a value less than a value of a heating power duty). In this manner, overheating of the heater 37 and the pump cell 20 due to the continuation (extension) of the temp rising control can be prevented.

Furthermore, in the embodiment, the extension time is set in accordance with an operating condition of the engine 11 and an environmental condition. In this manner, the extension time is changed in accordance with the time taken for the sensor cell 22 to achieve its activation temperature and thus can be set to an appropriate value; the time taken for the sensor cell 22 to achieve its activation temperature varies with an operating condition of the engine 11 (for example, coolant temperature) and an environmental condition (for example, outside air temperature).

Although in the embodiment described above, the extension time is set in accordance with both of an operating condition of the engine 11 and an environmental condition, this is not a limitation. The extension time may be set in accordance with one of an operating condition of the engine 11 and an environmental condition. Alternatively, the extension time may be a preset fixed value.

Moreover, although the extension period for the temp rising control is set in terms of time in the embodiment described above, this is not a limitation. The extension period for the temp rising control may be set in terms of, for example, any of the integral power consumption of the heater 37, and an integral exhaust flow quantity (or an integral intake flow quantity), the fuel injection count, and the ignition count of the engine 11.

The application of the present disclosure is not limited to a $NO_X$ sensor; it can be used for various exhaust gas sensors provided with a sensor element including a plurality of cells (for example, an air-fuel ratio sensor).

The invention claimed is:

1. A heater control device for an exhaust gas sensor disposed in an exhaust gas passage of an internal combustion engine and including a sensor element having a chamber through which gas exhausted from the internal combustion engine passes, a sensor cell that detects a concentration of a predetermined gas in the chamber, a pump cell to discharge or draw oxygen in the chamber, and a heater heating the pump cell and the sensor cell, the heater control device comprising:
 a storage medium which stores at least one computer program;
 a computer which executes the computer program so that the heater control device is configured to:
  execute a temperature rising control, in which an impedance of the pump cell is detected and a temperature of the pump cell and the sensor cell is raised until the impedance of the pump cell reaches a target impedance by setting a power control value of the heater as a heating power control value, wherein a temperature raising speed of the pump cell is higher than a temperature raising speed of the sensor cell,
  continue the temperature rising control until an extension period elapses that is needed for the sensor cell to reach an activation temperature after the impedance of the pump cell reaches the target impedance, and
  set the extension period when the impedance becomes smaller than the target impedance.

2. The heater control device according to claim 1, wherein the computer executes the computer program so that the heater control device is further configured to:
 set the extension period in accordance with at least one of an operating condition of the internal combustion engine and an environmental condition.

3. The heater control device according to claim 1, wherein the computer executes the computer program so that the heater control device is further configured to:
 determine that the exhaust gas passage is dry; and
 detect the impedance of the pump cell after determination that the exhaust gas passage is dry.

4. The heater control device according to claim 1, wherein when it is determined during the temperature rising control that one of the temperature of the heater and the temperature of the pump cell exceeds a corresponding predetermined temperature, the computer executes the computer program to interrupt the temperature rising control and sets the power control value of the heater to a value less than the heating power control value.

5. The heater control device according to claim 4, wherein the predetermined temperature is lower than an upper-limit temperature of the heater.

6. The heater control device according to claim 1, wherein when it is determined the impedance of the pump cell has a value equal to or less than a predetermined value, the computer executes the computer program to interrupt the temperature rising control and sets the power control value of the heater to a value less than the heating power control value.

7. The heater control device according to claim 1, wherein the heater at least partially overlaps with the sensor cell in a thickness direction of the sensor element and the heater also at least partially overlaps with the pump cell in the thickness direction of the sensor element.

* * * * *